(12) United States Patent
Smith

(10) Patent No.: US 7,391,849 B2
(45) Date of Patent: Jun. 24, 2008

(54) ENERGY MONITORING TARGET FOR X-RAY DOSE-RATE CONTROL

(75) Inventor: Richard R. Smith, San Ramon, CA (US)

(73) Assignee: Accuray Incorporated, Sunnyvale, CA (US)

( * ) Notice: Subject to any disclaimer, the term of this patent is extended or adjusted under 35 U.S.C. 154(b) by 38 days.

(21) Appl. No.: 11/411,259

(22) Filed: Apr. 25, 2006

(65) Prior Publication Data

US 2007/0248214 A1    Oct. 25, 2007

(51) Int. Cl.
*H05G 1/34* (2006.01)
(52) U.S. Cl. ......................... 378/109; 378/101
(58) Field of Classification Search ............ 378/65, 378/119, 121, 137, 138, 109, 110, 113; 250/305, 250/393, 396 R, 398, 492.1, 492.3, 505.1; 600/407, 411
See application file for complete search history.

(56) References Cited

U.S. PATENT DOCUMENTS 6,493,421 B2 * 12/2002 Gutman ..................... 378/84

2001/0015412 A1 * 8/2001 Komori et al. ........... 250/492.3

OTHER PUBLICATIONS

C.J. Karzmark Ph.D. and Robert J. Morton, M.S., "A Primer on Theory and Operation of Linear Accellerators in Radiation Therapy", Second Edition, Medical Physics Publishing, Copyright 1998, pp. 29 total (double-sided).

Alexander Wu Chao and Maury Tigner, "Handbook of Accelerator Physics and Engineering" 2nd Printing, Chapter 7 Subsystems, section 7.3 Acceleration, World Scientific Publishing Co. Pte. Ltd., Copyright 1999, pp. 49 total.

Coste-Manière, È., "Robotic whole body stereotactic radiosurgery: clinical advantages of the CyberKnife® integrated system", The International Journal of Medical Robotics +Computer Assisted Surgery, 2005, www.roboticpublications.com, pp. 28-39.

* cited by examiner

*Primary Examiner*—Courtney Thomas
(74) *Attorney, Agent, or Firm*—Blakely, Sokoloff, Taylor & Zafman LLP

(57) ABSTRACT

A target structure for an electron linear accelerator converts energy in an electron beam to x-rays and provides for the monitoring and control of the effective energy of the electron beam by collecting and processing a residual current in the target structure.

24 Claims, 9 Drawing Sheets

Figure 6A
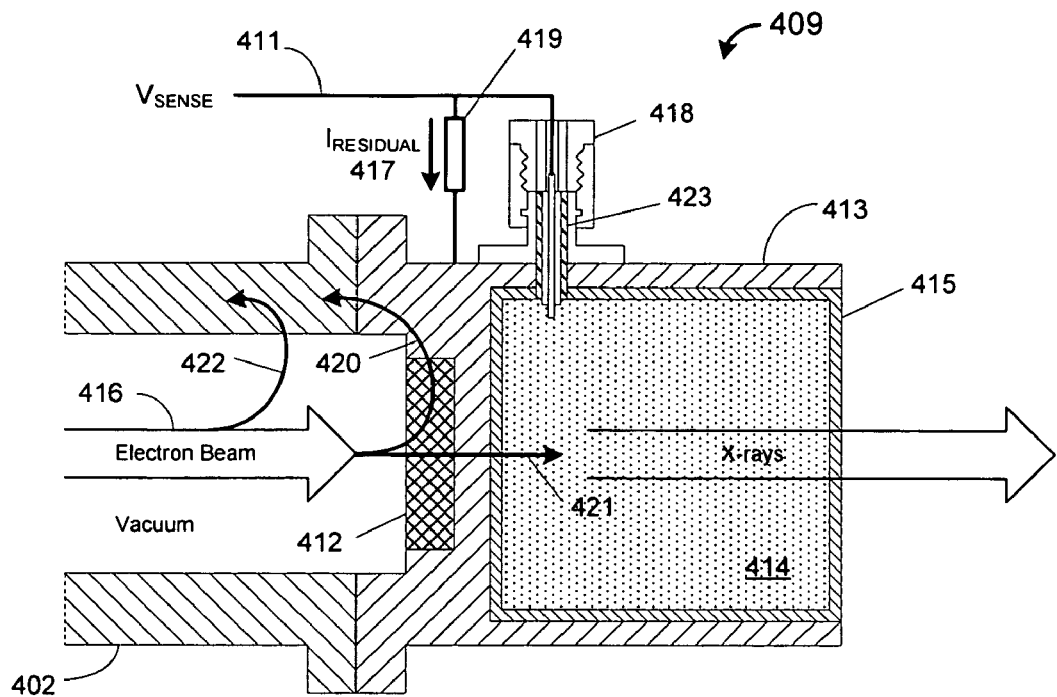
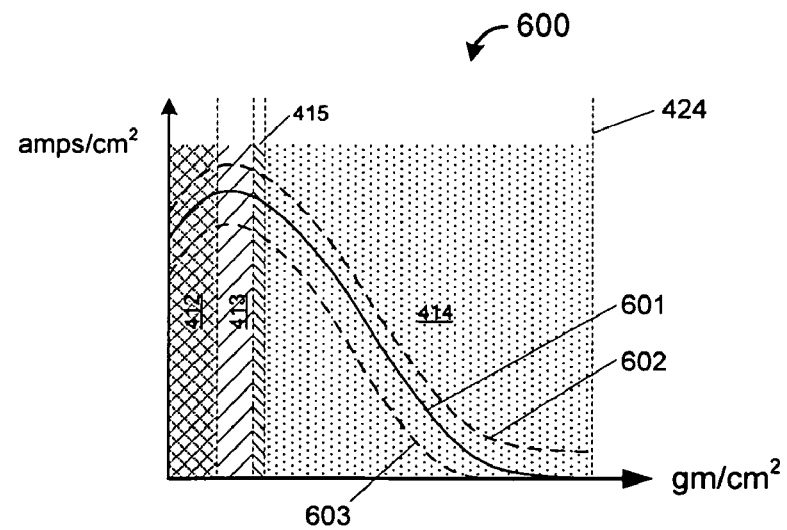
Figure 6B

ENERGY MONITORING TARGET FOR X-RAY DOSE-RATE CONTROL

TECHNICAL FIELD

Embodiments of the invention are related to the monitoring and control of energy levels in linear accelerator x-ray sources.

BACKGROUND

Radiosurgery and radiotherapy systems are radiation treatment systems that use external radiation beams to treat pathological anatomies (e.g., tumors, lesions, vascular malformations, nerve disorders, etc.) by delivering a prescribed dose of radiation (e.g., x-rays or gamma rays) to the pathological anatomy while minimizing radiation exposure to surrounding tissue and critical anatomical structures (e.g., the spinal chord). Both radiosurgery and radiotherapy are designed to necrotize the pathological anatomy while sparing healthy tissue and the critical structures.

Radiotherapy and radiosurgery systems include fixed-source gamma-ray treatment systems, and gantry-based and robotic-based x-ray treatment systems. In a fixed-source gamma-ray treatment system, multiple gamma ray beams from a distributed radioactive source (e.g., cobalt-60) are directed through bores in a hemispherical shield to a fixed point of convergence (isocenter). The patient is then moved relative to the isocenter to treat the pathology. In gantry-based x-ray systems, an x-ray beam source is attached to a gantry that moves around a center of rotation (isocenter) in a single plane. Each time an x-ray beam is delivered during treatment, the axis of the beam passes through the isocenter. As above, the patient is moved relative to the isocenter in order to treat the pathology. In robotic-based x-ray systems, the x-ray source has multiple degrees of freedom and the radiation treatment is not constrained to an isocenter.

In the x-ray treatment systems described above, the x-ray source is typically an electron linear accelerator (LINAC). A LINAC produces x-rays by bombarding a target with a high-energy electron beam. The x-rays are high-energy photons produced when the electron beam is intercepted by a target material having a high atomic number, such as tungsten for example. Two types of x-rays are produced. The first type is bremsstrahling (braking) radiation, given up by the electrons when they are slowed in the target. The second type is k-shell radiation, produced when atomic electrons transition between energy states after being excited by the bombarding electrons in the electron beam. Bremsstrahlung radiation produces a continuous energy spectrum, while k-shell radiation has an energy signature that is a function of the target material. X-rays are produced continuously through the cross-section of a target as a nonlinear function of electron beam current and energy.

In a LINAC, electrons from an electron gun at a negative potential are accelerated to the target, which is held at a positive potential relative to the electron gun (e.g., at a system ground potential). The electrons are accelerated through a waveguide accelerator structure by applying a sinusoidal radio frequency (RF) voltage to a series of evacuated, tuned cavities that form the structure. If the dimensions of the cavities and the frequency of the RF voltage have the proper relationship, the electrons experience an accelerating field, gaining velocity until they approach the speed of light, and then increasing their relativistic mass as they travel through the structure.

Radio frequency LINACs used for radiotherapy or radiosurgery applications typically employ either a traveling wave accelerator or a standing wave accelerator. In a traveling wave accelerator, the RF electric field launches from one end of the structure and travels to the other end, where the unused portion of the power is absorbed externally or internally to the structure. Electrons are accelerated by riding the crests of the RF electric field as it travels through the waveguide structure. In a standing wave accelerator, the RF electric field is allowed to reflect from the ends of the accelerator structure, setting up a standing wave pattern similar to that of a vibrating string. The pattern has stationary minima (nodes) centered in every other cavity and sinusoidally time-varying fields in the intervening cavities that oscillate between positive and negative maxima. Electrons are accelerated in a standing wave structure by receiving a "push" from the electric field in a cavity with a time-varying field, coasting through a cavity with a near-zero field node, and then arriving at the next cavity at the optimum time to receive the next "push." One variation of the standing wave accelerator includes the side-coupled standing wave accelerator. In a side-coupled standing wave accelerator, the nodal cavities (cavities with a near-zero RF field) are moved off axis and side-coupled with the accelerating cavities. This configuration allows the electrons to be continuously accelerated while shortening the overall length of the accelerator.

Conventional LINACS, such as those used in gantry-type radiosurgery systems, are S-Band designs (S-Band designates frequencies between 2 gigahertz and 4 gigahertz), typically operating at an RF frequency of approximately 3 gigahertz (3 GHz) and accelerating electrons to energies ranging from 4 to 20 million electron volts (MeV), with a typical value being approximately 6 Mev. At 3 Ghz, the RF cavities of the accelerator are relatively large, and the manufacturing tolerances of the RF cavities are relatively easy to meet. However, the accelerator, which is normally fabricated from copper for good electrical and thermal conductivity, is large and heavy. As a result, the LINAC requires rigid support within the gantry. FIG. 1 illustrates a cross-sectional schematic of a conventional gantry system 100. The LINAC 101 is mounted parallel to the axis of rotation of the gantry. A high power klystron oscillator 102, mounted in a stationary part of the system (stand 103), provides the 3 Ghz RF energy to the LINAC 101 through pressurized waveguides 104, a circulator 105 (to absorb energy reflected from the LINAC) and a rotating waveguide joint 106. The waveguide is pressurized by pressure system 107 with an insulating gas (e.g., sulfur hexafluoride) to prevent electrical breakdown in the waveguide from high RF electric fields. A water cooling system 108 provides temperature controlled water to the klystron and LINAC to maintain frequency stability. Temperature induced dimensional changes in the LINAC can detune the RF cavities and impair the acceleration process. Some systems also include an automatic frequency control (AFC) circuit 109 to fine tune the frequency of the klystron to match the optimum frequency of the LINAC. System 100 also includes a pulsed power supply 110 to synchronously pulse the klystron and the electron gun 111 in the LINAC. A remote control console 112 coordinates the overall functioning of the system.

Controlling the x-ray dose-rate and total radiation dose is important in medical LINAC applications, particularly in radiotherapy and radiosurgery where excessive radiation exposure can damage healthy tissue.

One conventional approach to controlling electron beam energy, used in the gantry system of FIG. 1, is the use of a magnetic field to bend and focus the electrons in a treatment head 115. FIG. 2 is a cross-sectional view of the treatment head 115. The treatment head includes a bending magnet assembly 116 that is coupled to the LINAC 101 and maintained at a vacuum with the LINAC by a vacuum system 113. Magnets in the bending magnet assembly (not shown) generate a magnetic field transverse to the path of the electron beam 117 as it exits the LINAC. The force exerted on an electron in a magnetic field is proportional to the charge of the electron, the vector velocity of the electron, and the vector magnetic field, and is directed at a 90 degree angle to both the magnetic field and the instantaneous trajectory of the electron. As a result, the electrons in the beam are bent in a 270 degree orbit and are directed downward when they strike the x-ray target 118. The strength and shape of the magnetic field is designed such that only those electrons in a specified energy range (i.e., velocity range) will strike the target and generate x-rays. Electrons with energies above or below the specified range take different trajectories and are intercepted by absorbing materials located outside of the target trajectory. Electrons exit the vacuum of the accelerator and bending assembly through a window 120 and strike the x-ray target 118. The x-ray beam then passes through an ionization chamber 121, where the ionization current produced by the x-rays provides an indirect measure of the radiation dose applied to the patient.

One problem in conventional systems is that the large number of electrons which exit the vacuum of the accelerator structure can interact with the ambient atmosphere of the operating room to generate ozone in collisions with oxygen molecules. Ozone is a powerful oxidizer, is corrosive to many common operating room materials and can cause lung irritation and damage in humans.

BRIEF DESCRIPTION OF THE DRAWINGS

The present invention is illustrated by way of example, and not by limitation, in the figures of the accompanying drawings in which:

FIG. 6A illustrates a LINAC assembly incorporating an energy monitoring target in one embodiment;

FIG. 6B illustrates a charge-depth profile of an energy monitoring target assembly in one embodiment.

DETAILED DESCRIPTION

Figure 1:
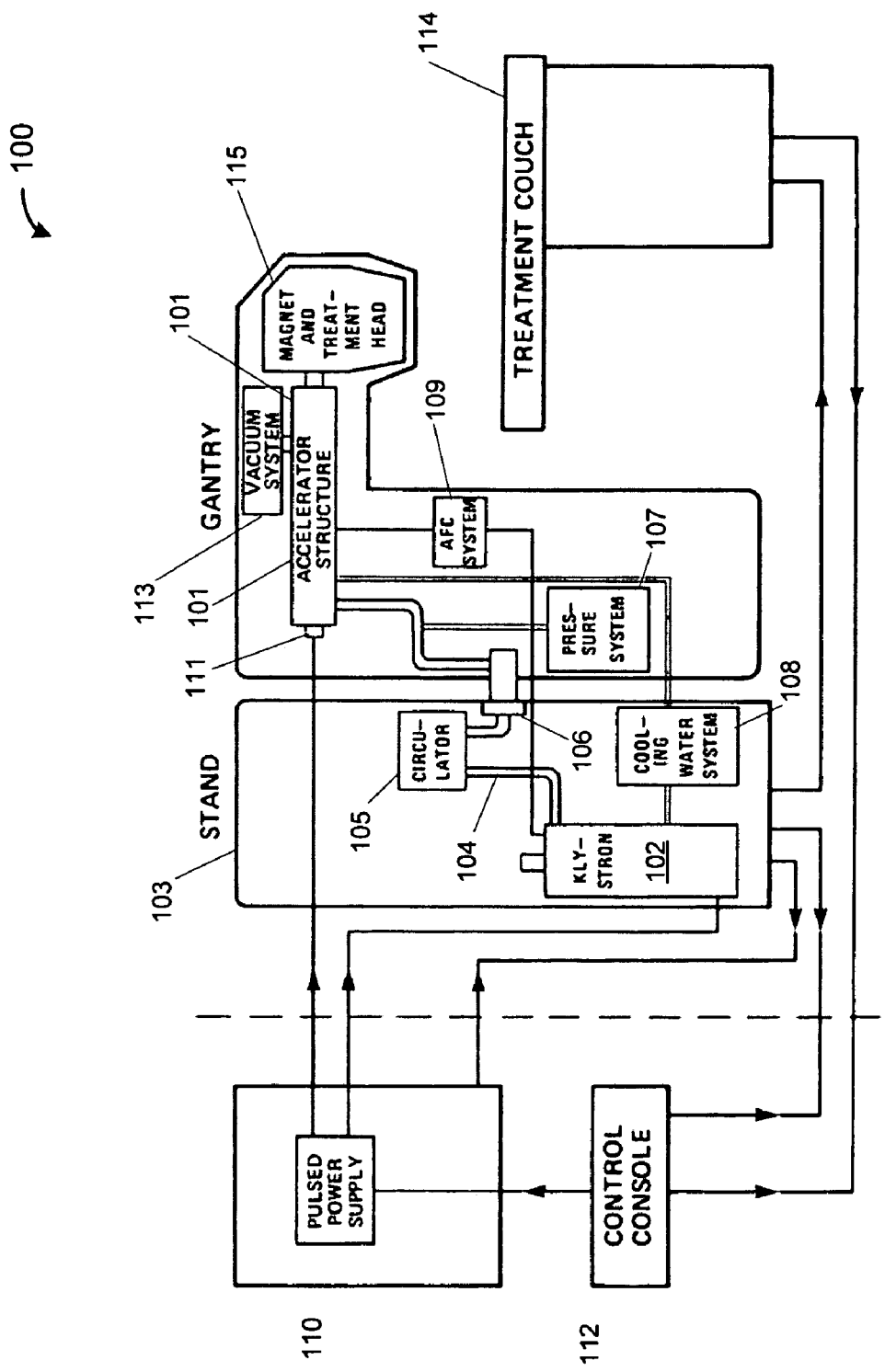
FIG. 1 illustrates a conventional radiation treatment system.
Figure 2:
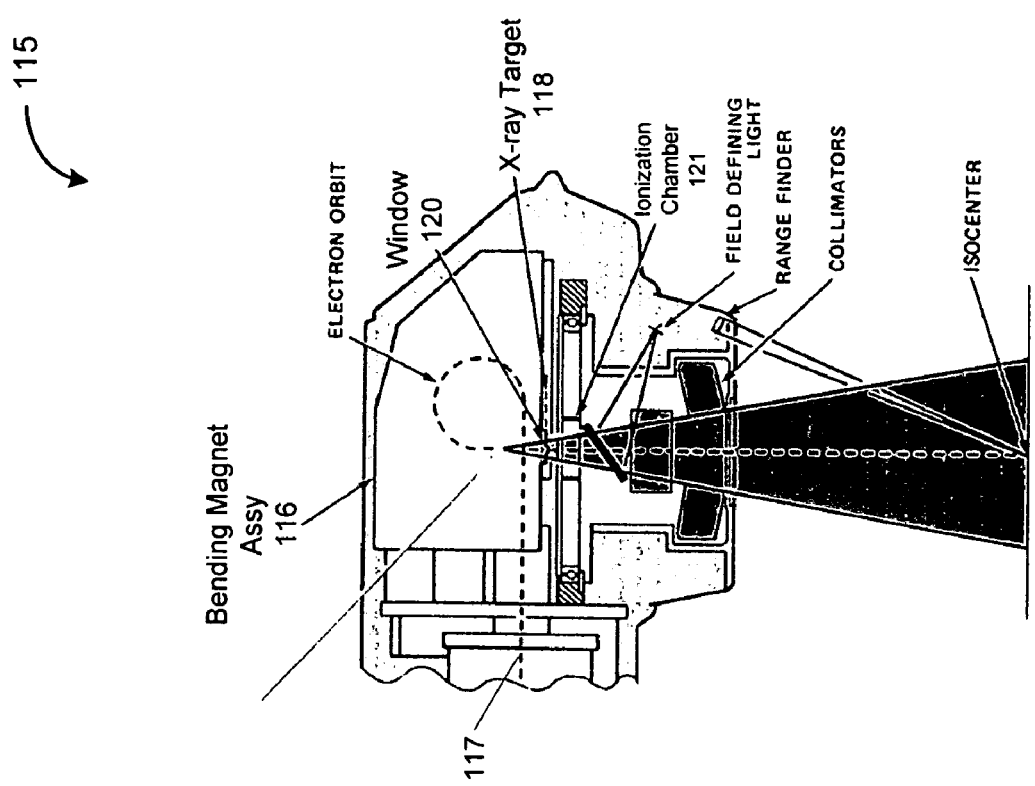
FIG. 2 illustrates a head assembly in a conventional radiation treatment system.

In the following description, for purposes of explanation, numerous specific details are set forth in order to provide a thorough understanding of the present invention. It will be evident, however, to one skilled in the art that the present invention may be practiced without these specific details. In other instances, well-known circuits, structures and techniques are not shown in detail or are shown in block diagram form in order to avoid unnecessarily obscuring an understanding of this description.

References throughout this specification to "one embodiment" or "an embodiment" means that a particular feature, structure or characteristic described in connection with the embodiment is included in at least one embodiment of the present invention. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the invention. In addition, while the invention has been described in terms of several embodiments, those skilled in the art will recognize that the invention is not limited to the embodiments described. The embodiments of the invention can be practiced with modification and alteration within the scope of the appended claims. The specification and the drawings are thus to be regarded as illustrative instead of limiting on the invention.

Methods and apparatus for determining and controlling the effective energy of an electron beam in a LINAC are described. In one embodiment, a method includes converting a portion of the energy in an electron beam to x-ray radiation, capturing a residual current of the electron beam and determining the effective energy of the electron beam from a ratio of the residual current to a source current of the electron beam.

In one embodiment, an apparatus includes a target to convert a portion of the energy in an electron beam to x-ray radiation, a collector coupled to the target to pass the x-ray radiation and to collect a residual current of the electron beam, and a sensor coupled with the collector to measure the residual current of the electron beam and to determine the energy level of the electron beam from a ratio of the residual current to the source current of the electron beam.

In the following description, embodiments of the invention are described in detail with respect to applications of the invention in the field of radiotherapy and radiosurgery. It will be appreciated, however, that embodiments of the invention may be practiced in other fields where LINAC's are used. LINAC's are used to generate x-rays for a variety of industrial, commercial and medical uses. For example, LINAC x-ray sources are used to perform non-destructive x-ray inspection and testing of valves in nuclear power plants and welds in building and bridge construction, detection of structural damage in airframes, detection of contraband (e.g., in vehicles and cargo), sterilization of medical products (e.g., bone grafts and transplants) and irradiation of food products.

Figure 3:
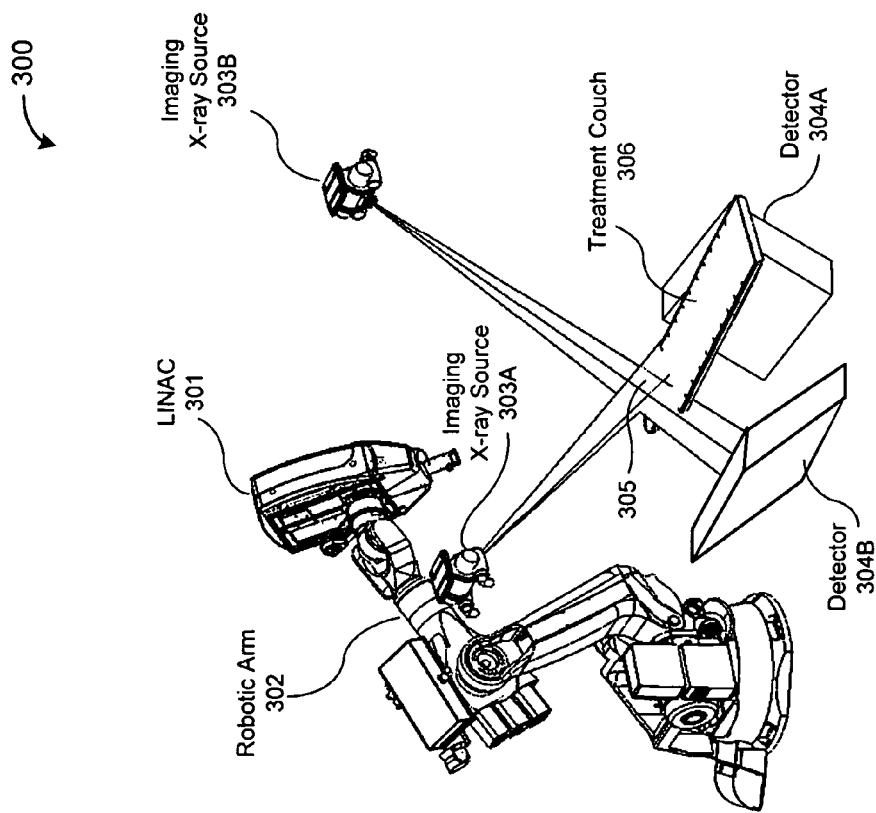
FIG. 3 illustrates a robotically controlled, image-guided radiation treatment system in one embodiment.

FIG. 3 illustrates the configuration of an image-guided, robotic-based radiation treatment system 300, having a LINAC assembly according to one embodiment of the present invention. In FIG. 3, the radiation treatment source is a LINAC 301 mounted on the end of a robotic arm 302 having multiple (e.g., 5 or more) degrees of freedom in order to position the LINAC 301 to irradiate a pathological anatomy (target region or volume) with beams delivered from many angles, in many planes, in an operating volume around the patient. Treatment may involve beam paths with a single isocenter, multiple isocenters, or with a non-isocentric approach (i.e., the beams need only intersect with the pathological target volume and do not necessarily converge on a single point, or isocenter, within the target).

In FIG. 3, the imaging system includes imaging X-ray sources 303A and 303B and X-ray detectors (imagers) 304A and 304B. Typically, the two imaging x-ray sources 303A and 303B are mounted in fixed positions on the ceiling of an operating room and are aligned to project imaging x-ray beams from two different angular positions (e.g., separated by 90 degrees) to intersect at a machine isocenter 305 (where the patient will be located during treatment on a treatment couch 306) and to illuminate imaging surfaces (e.g., amorphous silicon detectors) of respective detectors 304A and 304B after passing through the patient.

To achieve the light weight and compact size desirable in a robotic system, the LINAC 301 may operate in X-band (e.g., at an RF frequency between 8 GHz and 12.4 GHz) and, in one embodiment at approximately 9.3 GHz. The higher operating frequency, relative to a conventional (e.g., gantry-based) LINAC reduces the length of the accelerator by approximately a factor of three, for a given number of accelerating cavities, with a concomitant reduction in mass and weight. As a result, all of the essential components of a 6 Mev LINAC may be packaged in a relatively compact assembly, weighing approximately 150 kilograms (Kg), which may be mounted on the end of robotic arm 302. In one embodiment, LINAC 301 may include a standing wave accelerator structure, which may be a side-coupled cavity structure as is known in the art.

While embodiments of the invention may be described below in combination with an X-band LINAC, it will be appreciated that other embodiments of the invention may be implemented in combination with a conventional LINAC, such as the S-band LINAC described above.

Figure 4:
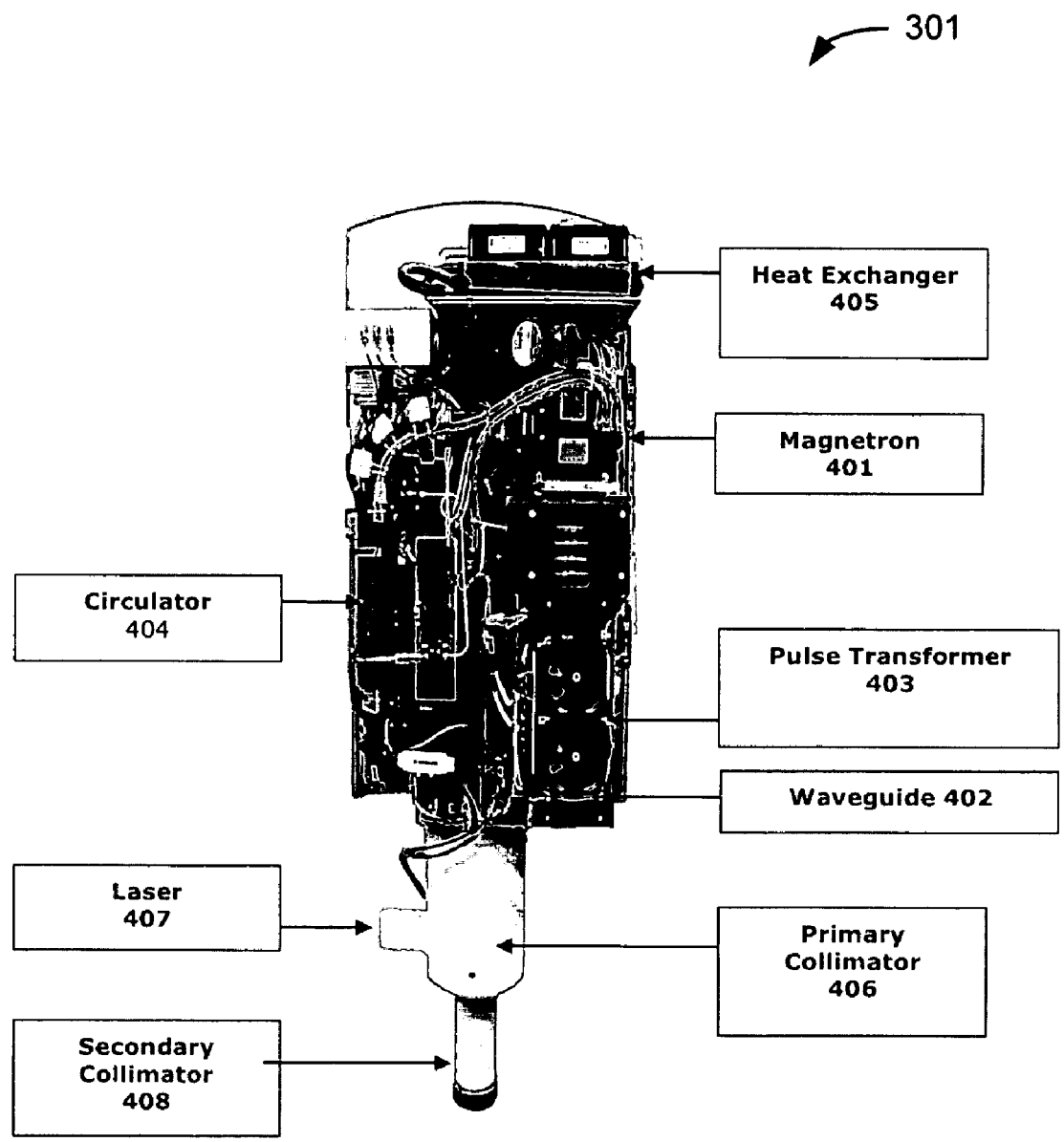
FIG. 4 illustrates a compact LINAC assembly in one embodiment.

FIG. 4 illustrates the arrangement of components within LINAC assembly 301 in one embodiment. LINAC assembly 301 includes a magnetron 401, which is a class of crossed-field microwave oscillator that may replace the klystron in a conventional LINAC. Magnetron 401 is coupled to the accelerator waveguide 402 through circulator 404 using rigid X-band waveguide in one embodiment. A pulse transformer 403 provides voltage pulses to the magnetron and to an electron gun (not shown in FIG. 4) attached to the waveguide, in a manner analogous to the conventional system. A heat exchanger 405 provides temperature controlled coolant to the waveguide and magnetron, which are provided with integral cooling jackets or lines as are known in the art. A remote cooling unit (not shown) is connected to the heat exchanger through the robotic arm 302 to remove heat from the LINAC and to control the operating temperature. A primary collimator 406 contains the energy monitoring target structure described in greater detail below, as well as a spotting laser 407, which may be used for x-ray beam alignment. The primary collimator and a secondary collimator 408 provide successive levels of beam shaping.

Figure 5:
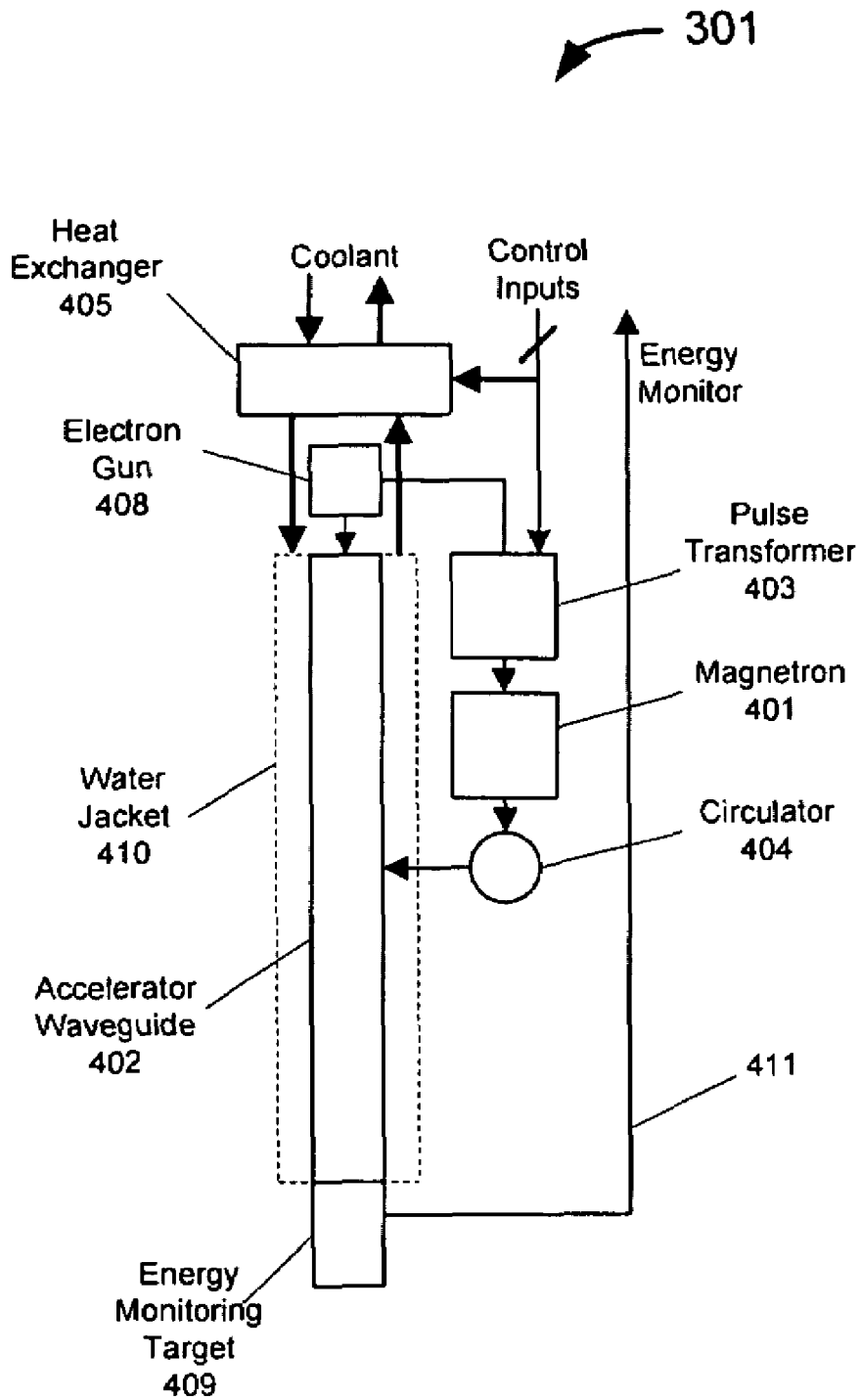
FIG. 5 is a block diagram illustrating the compact LINAC assembly of FIG. 4 in one embodiment.

FIG. 5 illustrates LINAC assembly 301 in a schematic, block diagram form. In FIG. 5, electron gun 408 supplies electrons to the accelerator and an energy monitoring target 409 converts the accelerated electrons into x-rays as described below and provides an energy monitor output 411. FIG. 5 also illustrates the closed loop heat exchange between a water jacket 410 and the heat exchanger 405 as described above.

FIG. 6A illustrates a cross-section of an energy monitoring target structure 409 in one embodiment, coupled to the waveguide cavity structure 402 (partially shown). In one embodiment, target structure 409 may have a cylindrical body that conforms with collimator 406, for example. Target structure 409 includes a target 412 to perform the principal conversion of electron energy to x-rays. Target 412 may be, for example, an alloy of tungsten and rhenium where the tungsten is the principle source of x-rays and the rhenium provides thermal and electrical conductivity. In general, the target may include one or more target materials having an atomic number approximately greater than or equal to 70 to provide efficient x-ray generation.

The electron beam 416 may be characterized by an average or effective energy rate that is equal to the total energy divided by the number of electrons in the beam per unit time. However, individual electrons in electron beam 416 will, in general, fall into a range of energies determined by the design of the LINAC, the frequency and power of the RF energy source (e.g., magnetron 401), and the cathode to anode voltage. When electrons from the electron beam 416 enter the target 412, they give up energy in the form of heat and x-rays (photons), and lose velocity. The x-rays thus produced will also have an energy distribution related to the initial energies of the electrons, and to the composition and thickness of the target material. In one embodiment, the thickness of target 412 in the direction of the electron beam 416 may be selected to be approximately 40% of the thickness required to reduce the energy of an average electron to zero. Limiting the thickness of the target 412 limits the range of the energy distribution of the x-rays and, in particular, reduces the production of low energy photons. In a radiosurgery application, low energy photons can increase the radiation exposure of healthy tissue without being effective against a targeted pathological anatomy.

Target 412 may be mounted in a metallic holder 413, which may be a good thermal and electrical conductor such as copper, for example. Holder 413 may be coupled to the waveguide cavity structure 402 with a vacuum tight seal and the waveguide structure, including the target area, may be evacuated. Holder 413 may also provide a receptacle for an electron collector 414 to collect electrons that are not stopped within and/or that are generated within target 412, and that exit target 412. Collector 414 may be a block of electron absorbing material, which may be a conductive graphite based compound, for example. In general, collector 414 may be made of one or more materials with an atomic number approximately less than or equal to 6 to provide both electron absorption and transparency to x-rays generated by target 412. Collector 414 may be electrically isolated from holder 413 by an insulating layer 415. Insulating layer 415 may be an anodized aluminum layer, for example. The collector 414 may be provided with an external return path to holder 413 via a tapping connector 418 and a sensor 419, which may be a sense resistor, for example. Electrons collected in the collector 414 are thereby returned to the electron gun 408 via a ground return path as a residual current 417. The residual current 417 generates a sense voltage $V_{SENSE}$ across sensor 419 that is proportional to the residual current and which can be monitored on sense line 411.

The residual current 417 may be compared (e.g., via sense voltage $V_{SENSE}$) with the source current of the electron beam 416 provided by electron gun 408 to determine the effective energy of the electron beam. In one embodiment, the ratio of the residual current to the source current provides a measure to determine the effective energy of the electron beam for a given level of RF input power to the accelerator structure 402. Given the effective energy of the electron beam, the effective energy of the x-rays may be determined by calibrating the target structure design using methods known in the art. For example, during manufacture, the effective energy of an electron beam may be determined from an ionization profile created by the beam in a standardized water tank. The electron beam may then be used to generate x-rays in a sample target structure, and the same water tank may then be used to determine the effective x-ray energy from the ionization profile produced by the x-rays. The target structure design may then be characterized with a conversion factor that relates x-ray energy to electron beam energy.

In operation, an accelerated electron beam 416 impinges on target 412, generating bremsstrahling and k-shell x-rays as described above. Electrons 420 that are stopped within the target 412 are returned through ground (e.g., the body of the linear accelerator 402) to the electron gun 408 through the holder 413 and the accelerator structure 402. Beam electrons that pass through the target, and any secondary electrons generated within the target (collectively electrons 421), then pass through a thin cross-section of holder 413 and are absorbed as the residual current 417 in the collector and returned to the electron source through tap connector 418 and sensor 419. In practice, some percentage of beam electrons 422 impinge the accelerator waveguide structure 402 before they can strike the target 412. Therefore, the total source current of the electron beam 416 is returned to the electron gun via 1) a primary return path 420 though the target 412 and waveguide 402, 2) a secondary return path 421 through the collector 414, the sensor 419, the holder 413 and the waveguide 402, and 3) a tertiary return path through the waveguide 402 for electrons which do not strike the target 412.

Tap connector 418 may be a threaded connector as illustrated in FIG. 6A, or any other convenient connector or connectorless (e.g., directly soldered, welded or otherwise bonded) interface, as is known in the art. The connection with collector 414 may be accomplished, for example, with a section of coaxial cable, such as 0.085 inch semi-rigid cable 423 having a center conductor, insulating dielectric and outer conductor. Any other connection methods as are known in the art may also be used.

FIG. 6B illustrates a charge-depth chart 600 corresponding to the target structure of FIG. 6A. Charge-depth curve 601 plots electron current flux in amperes per square centimeter versus the average integrated mass density of the target structure, in grams per square centimeter, as a function of distance through the target structure 409. Target structure 409 may be configured to reduce the electron flux at the boundary 424 of the collector 414 to zero when the effective energy of the electron beam 416 is optimized, such that the x-ray dose rate is nominal (i.e., the desired level) and no free electrons exit the target structure to generate stray radiation and/or produce ozone. The residual current 417 (as represented by $V_{SENSE}$, for example), which is proportional to the area under charge-depth curve 601, may be compared with the source current of the electron beam 416, as described above, to determine the effective energy of the electron beam. For a given source current, the energy of the electron beam and the ratio of the residual current to the source current increases as the RF input power to the LINAC is increased. Conversely, the energy of the electron beam and the ratio of the residual current to the source current decrease as the RF input power to the LINAC is decreased. Therefore, once the target structure has been characterized as described above, the residual current may be used to control the energy of the electron beam by controlling the RF input power to the LINAC, as described in greater detail below.

Charge-depth curve 602 illustrates an exemplary electron current flux distribution when the effective energy of the electron beam is too high. In the example of curve 602, the electron flux is non-zero at the boundary 424 of collector 414, and the total x-ray dose rate (approximately proportional to the peak value of the charge-depth curve) is above nominal. Conversely, charge-depth curve 603 illustrates an exemplary electron current flux distribution when the effective energy of the electron beam is too low. The peak value of the charge-depth curve is below the nominal value represented by curve 601 and the electron current flux reaches zero well before the boundary 424 of the collector 414. Either condition (i.e., too much energy or too little energy) may be detected by measuring the value of $V_{SENSE}$. As noted above, the value of $V_{SENSE}$ is proportional to the residual current 417, and the residual current is proportional to the area under the depth-charge curve (e.g., curves 601, 602 and 603) in collector 414. Therefore, a change in residual current 417, reflecting a change in the effective energy of the electron beam, may be used in a control feedback loop to control the RF input level to the accelerator structure to control the effective energy of the electron beam.

Figure 6C:
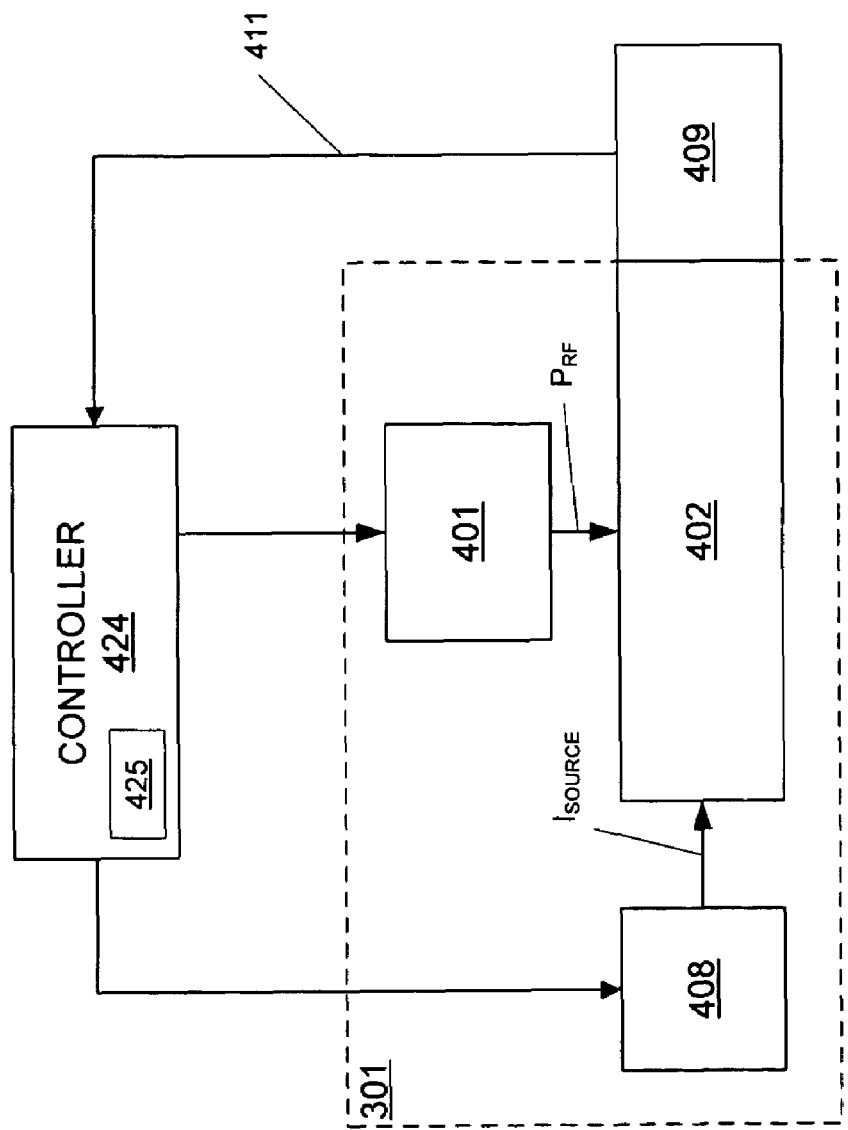
FIG. 6C illustrates a feedback control loop in one embodiment.

FIG. 6C illustrates a feedback control loop in one embodiment. In the embodiment of FIG. 6C, target structure 409 generates a sense voltage $V_{SENSE}$ on sense line 411 that may be detected by a controller 424. Controller 424 may be any type of controller or processing device as is known in the art. Controller 424 may be coupled to electron gun 408 and magnetron 401. Controller 424 may be configured to sense and control the source current $I_{SOURCE}$ of the electron beam provided to accelerator structure 402 by electron gun 408. Controller 424 may also be configured to control the RF power $P_{RF}$ supplied to accelerator structure 402 by magnetron 401. Controller 424 may include calibration tables (e.g., lookup tables) 425, containing calibration data for LINAC 301 and target structure 409, which may be used to control the effective energy of electron beam 416. For example, calibration tables 425 may contain tables of effective electron beam energy versus $P_{RF}$ and values of $I_{SOURCE}$ and $V_{SENSE}$ (representing values of the residual current 417).

Figure 7:
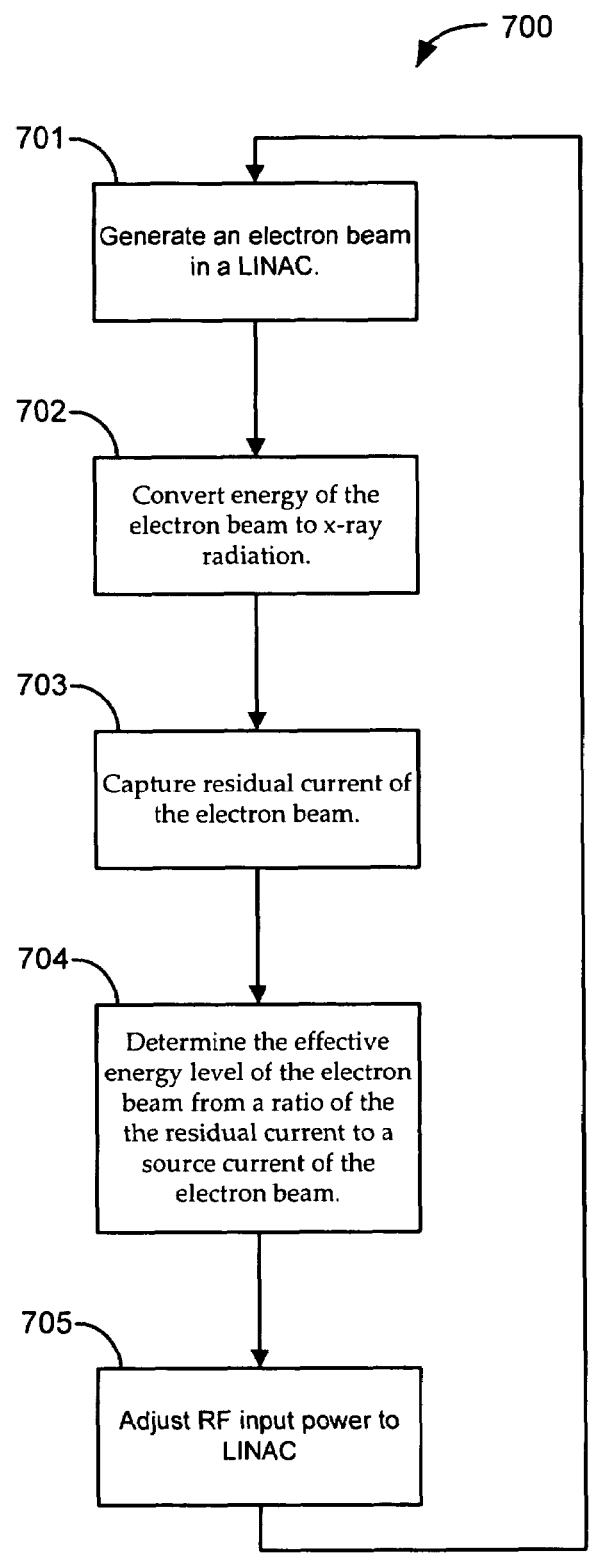
FIG. 7 is a flowchart illustrating one embodiment of a method of energy monitoring in a radiation treatment system.

FIG. 7 is a flowchart illustrating a method 700 of electron beam energy monitoring and/or control in one embodiment. At operation 701, an electron beam (416) is generated in a LINAC (301) as described above. At operation 702, energy in the electron beam is converted to x-ray radiation in target structure 409. At operation 703, residual current (417) is captured by a collector (414) and returned to a source of electron beam current (408) through a sensor (419). At operation 704, the effective energy level of the electron beam (416) is determined (e.g., by a controller such as controller 424) from a ratio of the residual current 417 to a source current of the electron beam. At operation 705, the effective energy of the electron beam is maintained and/or corrected by adjusting an RF input power level to the LINAC. The operations 701 through 705 may be repeated on a continuous basis to maintain control of the effective energy level of the electron beam.

Figure 8:
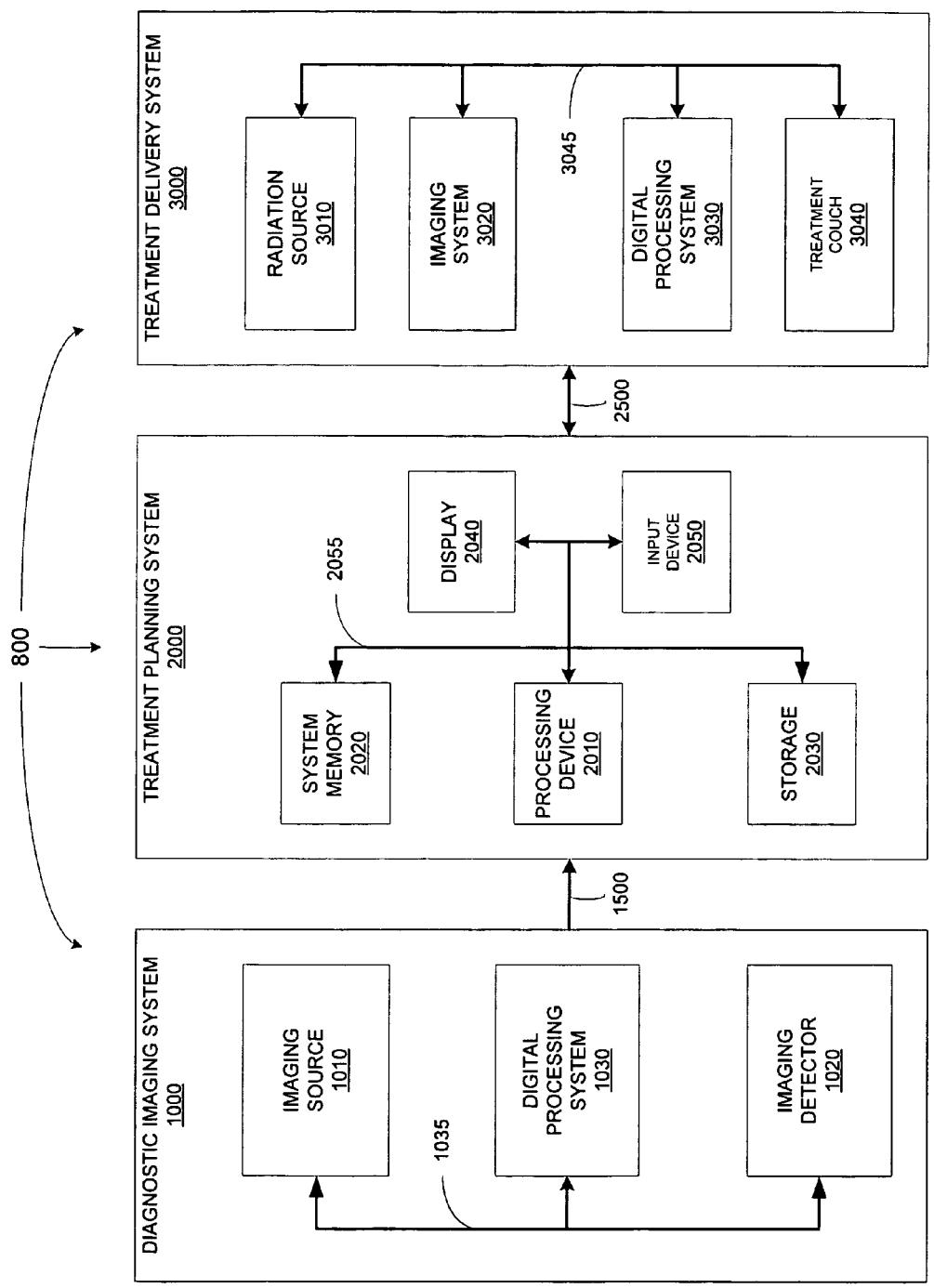
FIG. 8 illustrates a system in which embodiments of the present invention may be implemented.

FIG. 8 illustrates one embodiment of systems that may be used in performing radiation treatment in which features of the present invention may be implemented. As described below and illustrated in FIG. 8, system 800 may include a diagnostic imaging system 1000, a treatment planning system 2000 and a treatment delivery system 3000.

Diagnostic imaging system 1000 may be any system capable of producing medical diagnostic images from a 3-D volume study of a volume of interest (VOI) in a patient, that may be used for subsequent medical diagnosis, treatment planning and/or treatment delivery. For example, diagnostic imaging system 1000 may be a computed tomography (CT) system, a magnetic resonance imaging (MRI) system, a positron emission tomography (PET) system, an ultrasound system or the like. For ease of discussion, diagnostic imaging system 1000 may be discussed below, at times, in terms of a CT imaging modality. However, other imaging modalities such as those above may also be used.

Diagnostic imaging system 1000 includes an imaging source 1010 to generate an imaging beam (e.g., x-rays, ultrasonic waves, radio frequency waves, etc.) and an imaging detector 1020 to detect and receive the beam generated by imaging source 1010, or a secondary beam or emission stimulated by the beam from the imaging source (e.g., in an MRI or PET scan). In one embodiment, diagnostic imaging system 1000 may include one or more diagnostic X-ray sources and one or more corresponding imaging detectors capable of generating 2-D radiographic images, in small angular increments, which may be used to construct 3-D images (e.g., a cone-beam CT scanner). For example, two x-ray sources may be disposed around a patient to be imaged, fixed at an angular separation from each other (e.g., 90 degrees, 45 degrees, etc.) and aimed through the patient toward (an) imaging detector(s) which may be diametrically opposed to the x-ray sources. A single large imaging detector, or multiple imaging detectors, can also be used that would be illuminated by each x-ray imaging source. Alternatively, other numbers and configurations of diagnostic imaging sources and imaging detectors may be used.

The imaging source 1010 and the imaging detector 1020 may be coupled to a digital processing system 1030 to control the imaging operation and process image data. Diagnostic imaging system 1000 includes a bus or other means 1035 for transferring data and commands among digital processing system 1030, imaging source 1010 and imaging detector 1020. Digital processing system 1030 may include one or more general-purpose processors (e.g., a microprocessor), special purpose processor such as a digital signal processor (DSP) or other type of device such as a controller or field programmable gate array (FPGA). Digital processing system 1030 may also include other components (not shown) such as memory, storage devices, network adapters and the like. Digital processing system 1030 may be configured to generate digital diagnostic images in a standard format, such as the DICOM (Digital Imaging and Communications in Medicine) format, for example. In other embodiments, digital processing system 1030 may generate other standard or non-standard digital image formats. Digital processing system 1030 may transmit diagnostic image files (e.g., the aforementioned DICOM formatted files) to treatment planning system 2000 over a data link 1500, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 2000 includes a processing device 2010 to receive and process image data. Processing device 2010 may represent one or more general-purpose processors (e.g., a microprocessor), special purpose processor such as a digital signal processor (DSP) or other type of device such as a controller, application specific integrated circuit (ASIC) or field programmable gate array (FPGA). Processing device 2010 may be configured to execute instructions for performing treatment planning operations discussed herein.

Treatment planning system 2000 may also include system memory 2020 that may include a random access memory (RAM), or other dynamic storage devices, coupled to processing device 2010 by bus 2055, for storing information and instructions to be executed by processing device 2010. System memory 2020 also may be used for storing temporary variables or other intermediate information during execution of instructions by processing device 2010. System memory 2020 may also include a read only memory (ROM) and/or other static storage device coupled to bus 2055 for storing static information and instructions for processing device 2010.

Treatment planning system 2000 may also include storage device 2030, representing one or more storage devices (e.g., a magnetic disk drive or optical disk drive) coupled to bus 2055 for storing information and instructions. Storage device 2030 may be used for storing instructions for performing the treatment planning steps discussed herein.

Processing device 2010 may also be coupled to a display device 2040, such as a cathode ray tube (CRT) or liquid crystal display (LCD), for displaying information (e.g., a 2D or 3D representation of the VOI) to the user. An input device 2050, such as a keyboard, may be coupled to processing device 2010 for communicating information and/or command selections to processing device 2010. One or more other user input devices (e.g., a mouse, a trackball or cursor direction keys) may also be used to communicate directional information, to select commands for processing device 2010 and to control cursor movements on display 2040.

It will be appreciated that treatment planning system 2000 represents only one example of a treatment planning system, which may have many different configurations and architectures, which may include more components or fewer components than treatment planning system 2000 and which may be employed with the present invention. For example, some systems often have multiple buses, such as a peripheral bus, a dedicated cache bus, etc. The treatment planning system 2000 may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view dose distributions on any one of various imaging modalities (e.g., MRI, CT, PET, etc.). Treatment planning systems are known in the art; accordingly, a more detailed discussion is not provided.

Treatment planning system 2000 may share its database (e.g., data stored in storage device 2030) with a treatment delivery system, such as treatment delivery system 3000, so that it may not be necessary to export from the treatment planning system prior to treatment delivery. Treatment planning system 2000 may be linked to treatment delivery system 3000 via a data link 2500, which may be a direct link, a LAN link or a WAN link as discussed above with respect to data link 1500. It should be noted that when data links 1500 and 2500 are implemented as LAN or WAN connections, any of diagnostic imaging system 1000, treatment planning system 2000 and/or treatment delivery system 3000 may be in decentralized locations such that the systems may be physically remote from each other. Alternatively, any of diagnostic imaging system 1000, treatment planning system 2000 and/or treatment delivery system 3000 may be integrated with each other in one or more systems.

Treatment delivery system 3000 includes a therapeutic and/or surgical radiation source 3010 (e.g., LINAC 301 including target structure 409) to administer a prescribed radiation dose to a target volume in conformance with a treatment plan. Treatment delivery system 3000 may also include an imaging system 3020 to capture in-treatment images of a patient volume (including the target volume) for registration or correlation with the diagnostic images described above in order to position the patient with respect to the radiation source. Treatment delivery system 3000 may also include a digital processing system 3030 (which may include a controller such as controller 424) to monitor and control an effective energy level in radiation source 3010 as described above, an imaging system 3020 and a patient support device such as a treatment couch 3040. Digital processing system 3030 may include one or more general-purpose processors (e.g., a microprocessor) or special purpose processors such as a digital signal processor (DSP) or other type of device such as an application specific integrated circuit (ASIC) or field programmable gate array (FPGA). Digital processing system 3030 may also include other components (not shown) such as memory, storage devices, network adapters and the like. Digital processing system 3030 may be coupled to radiation source 3010, imaging system 3020 and treatment couch 3040 by a bus 3045 or other type of control and communication interface.

Digital processing system 3030 may also implement methods (e.g., such as method 700 described above) to determine the energy level of electron beam 416 in LINAC 301 in order to monitor and control x-ray dose-rates during treatment.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the application of radiation beam(s). In one embodiment, for example, the apparatus described herein may be used in an industrial imaging system where the greatest penetration of x-rays is desired subject to the constraint that the co-production of photo-neutrons in radiation shielding material is minimized. Such an objective may be obtained, for example, by limiting the energy of accelerated electrons to 9 MeV where the probability of photo-neutron release is low.

It will be apparent from the foregoing description that aspects of the present invention may be embodied, at least in part, in software. That is, the techniques may be carried out in a computer system or other data processing system in response to its processor, such as processing device 2010 or digital processing system 3030, executing sequences of instructions contained in a memory, such as system memory 2020. In various embodiments, hardware circuitry may be used in combination with software instructions to implement the present invention. Thus, the techniques are not limited to any specific combination of hardware circuitry and software or to any particular source for the instructions executed by the data processing system. In addition, throughout this description, various functions and operations may be described as being performed by or caused by software code to simplify description. However, those skilled in the art will recognize what is meant by such expressions is that the functions result from execution of the code by a processor or controller, such as processing device 2010 or digital processing system 3030.

A machine-readable medium can be used to store software and data which when executed by a data processing system causes the system to perform various methods of the present invention. This executable software and data may be stored in various places including, for example, system memory 2020 and storage 2030 or any other device that is capable of storing software programs and/or data.

Thus, a machine-readable medium includes any mechanism that provides (i.e., stores and/or transmits) information in a form accessible by a machine (e.g., a computer, network device, personal digital assistant, manufacturing tool, any device with a set of one or more processors, etc.). For example, a machine-readable medium includes recordable/non-recordable media (e.g., read only memory (ROM); random access memory (RAM); magnetic disk storage media; optical storage media; flash memory devices; etc.), as well as electrical, optical, acoustical or other forms of propagated signals (e.g., carrier waves, infrared signals, digital signals, etc.); etc.

What is claimed is:

1. An apparatus, comprising:
    a target to convert energy of an electron beam to x-ray radiation;
    a collector coupled to the target to pass the x-ray radiation and to collect residual current of the electron beam;
    a sensor coupled to the collector to measure the residual current of the electron beam; and
    a processing device coupled to the sensor to determine an effective energy of the electron beam from a ratio of the residual current to a source current of the electron beam.

2. The apparatus of claim 1, further comprising a target holder, wherein the target holder is electrically and thermally coupled to the target, and wherein the target holder is mechanically coupled with the collector and electrically insulated from the collector.

3. The apparatus of claim 2, wherein the collector is electrically insulated from the target holder by an anodized aluminum enclosure.

4. The apparatus of claim 3, wherein the processing device is configured to control the effective energy of the electron beam via a feedback control loop to an RF power source of the electron beam.

5. The apparatus of claim 2, wherein the target holder comprises a primary return path for the electron beam and the sensor comprises a secondary return path for the electron beam.

6. The apparatus of claim 2, further comprising a linear accelerator to generate the electron beam, wherein the linear accelerator is coupled to the target holder with a vacuum seal, and wherein the target is disposed within a vacuum chamber.

7. The apparatus of claim 5, wherein the linear accelerator comprises a tertiary return path for the electron beam, and where the sum of currents in the primary, secondary and tertiary return paths is approximately equal to the source current of the electron beam.

8. The apparatus of claim 2, wherein the target comprises one or more target materials each having an atomic number approximately greater than or equal to 70, and wherein the collector comprises one or more electron absorbing materials each having an atomic number approximately less than or equal to 6.

9. The apparatus of claim 8, wherein the target comprises a combination of tungsten and rhenium and the collector comprises graphite.

10. A system, comprising:
    a linear accelerator to generate an electron beam;
    a target structure to generate x-rays from the electron beam, the target structure including a collector to collect a residual current of the electron beam while passing the x-rays;
    a sensor coupled with the collector to measure the residual current of the electron beam; and
    a processing device coupled with the sensor to determine an effective energy level of the electron beam from a ratio of the residual current to a source current of the electron beam.

11. The system of claim 10, wherein the processing device is configured to control the effective energy of the electron beam.

12. The system of claim 10, wherein the collector is configured to absorb residual electrons before the residual electrons exit the target structure.

13. An apparatus, comprising:
means for converting energy of an electron beam to x-ray radiation;
means for collecting a residual current of the electron beam; and
means for determining an effective energy of the electron beam from a ratio of the residual current to a source current of the electron beam.

14. The apparatus of claim 13, further comprising:
means for generating the electron beam; and
means for controlling the effective energy of the electron beam.

15. A method in a linear accelerator, comprising:
converting energy of an electron beam to x-ray radiation;
collecting a residual current of the electron beam; and
determining an effective energy of the electron beam from a ratio of the residual current to a source current of the electron beam.

16. The method of claim 15, further comprising:
generating the electron beam; and
controlling the effective energy of the electron beam.

17. The method of claim 15, further comprising determining an effective energy level of the x-ray radiation from the effective energy of the electron beam.

18. The method of claim 16, wherein controlling the effective energy of the electron beam comprises adjusting an RF power source of the linear accelerator in a feedback control loop.

19. The method of claim 16, wherein controlling the effective energy of the electron beam comprises minimizing electron leakage and scattered x-ray radiation.

20. An article of manufacture comprising:
a machine-accessible medium including data that, when accessed by a machine, cause the machine to perform operations comprising:
converting energy of an electron beam to x-ray radiation;
collecting a residual current of the electron beam; and
determining an effective energy of the electron beam from a ratio of the residual current of the electron to a source current of the electron beam.

21. The article of manufacture of claim 20, wherein the machine-accessible medium further includes data that cause the machine to perform operations comprising:
generating the electron beam; and
controlling the effective energy of the electron beam.

22. The article of manufacture of claim 20, wherein the machine-accessible medium further includes data that cause the machine to perform operations comprising determining an effective energy level of the x-ray radiation from the effective energy of the electron beam.

23. The article of manufacture of claim 21, wherein controlling the effective energy of the electron beam comprises adjusting an RF power source of a linear accelerator in a feedback control loop.

24. The article of manufacture of claim 21, wherein controlling the effective energy of the electron beam comprises minimizing electron leakage and scattered x-ray radiation.

* * * * *